United States

Porret et al.

[11] 3,971,813

[5] July 27, 1976

[54] GLYCIDYL COMPOUNDS CONTAINING PHOSPHORUS

[75] Inventors: Daniel Porret, Binningen; Jürgen Habermeier, Pfeffingen; Dieter Baumann, Birsfelden, all of Switzerland

[73] Assignee: Ciba-Geigy Corporation, Ardsley, N.Y.

[22] Filed: Oct. 9, 1973

[21] Appl. No.: 404,835

[30] Foreign Application Priority Data
Oct. 13, 1972  Switzerland.................... 15041/72

[52] U.S. Cl. ..................... 260/309.5; 106/15 FP; 260/63 R; 260/258; 260/260; 260/309.2; 260/309.7
[51] Int. Cl.² ..................................... C07D 233/02
[58] Field of Search .................................. 260/309.5

[56] References Cited

UNITED STATES PATENTS

| | | | |
|---|---|---|---|
| 3,562,275 | 2/1971 | Habermeier et al. | 260/260 |
| 3,780,056 | 12/1973 | Singhal et al. | 260/309.5 |
| 3,839,335 | 10/1974 | Gorbaty | 260/257 |

*Primary Examiner*—Henry R. Jiles
*Assistant Examiner*—C. M. S. Jaisle
*Attorney, Agent, or Firm*—Vincent J. Cavalieri

[57] ABSTRACT

Adducts of cyclic urea derivatives and dialkyl phosphites, containing glycidyl groups, for example adducts of a diglycidyl compound of hydantoins, substituted in the 5-position by alkyl groups or an alkylene group, and of diethyl phosphite or dimethyl phosphite. These adducts are used for the manufacture of flame-retarding plastics.

3 Claims, No Drawings

GLYCIDYL COMPOUNDS CONTAINING PHOSPHORUS

The invention relates to adducts of cyclic urea derivatives and dialkyl phosphites, containing glycidyl groups, and to their use for the manufacture of flame-retarding plastics.

Flame-retarding curable mixtures of epoxide compounds which consist at least partially of reaction products of dialkyl phosphites and polyepoxides, and curing agents for epoxide resins, are already known, for example from Swiss Patent Specification No. 456,949. However, the addition reaction of the alkyl phosphites with the epoxide compounds does not go to completion, so that in spite of very long reaction times the yield of the addition products is low. It has now been found that the new adducts can be manufactured easily and in high yield and furthermore lead to plastics which possess even better flame resistance than the known plastics.

The adducts according to the invention are reaction products, containing epoxide groups, of cyclic urea derivatives containing glycidyl groups, and compounds of the formula I

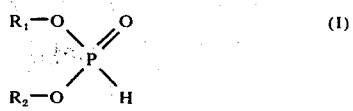

in which $R_1$ and $R_2$ each represent an alkyl or alkenyl group which can be substituted or together represent an alkylene group with 2 to 5 carbon atoms.

Preferably, the radicals $R_1$ and $R_2$ denote alkyl groups with 1 to 4 carbon atoms, especially the methyl, ethyl, propyl or monochloroethyl group.

Numerous compounds can be used as polyglycidyl compounds of cyclic ureides, examples being the diglycidyl compounds of ethyleneurea, of hydantoins, substituted in the 5-position by alkyl groups with 1–4 carbon atoms or by an alkylene group with 4–5 carbon atoms, of parabanic acid, barbituric acid, uracils and optionally dihydrouracils, of bis-hydantoin compounds linked via an aliphatic, cycloaliphatic or araliphatic group, of benzimidazolones or of their tetrahydro or hexahydro derivatives. The glycidyl groups can be directly bonded to the nitrogen atoms of the heterocyclic structures or can be bonded via a hydroxyalkyl group linked to the nitrogen atoms of the heterocyclic structures. Such diglycidyl compounds are described, for example, in the following patent specifications: GB 1,148,570, GB 1,165,060, GB 1,191,544, BE 744,846, FR 2,066,567, BE 759,863, BE 762,253, FR 2,089,854, BE 767,528, FR 2,000,334 and GB 1,260,892.

Triglycidyl compounds can also be used, for example triglycidylisocyanurate and triglycidyl derivatives of binuclear ureides, which are described in Belgian Patent Specification No. 782,032.

The new glycidyl compounds containing phosphorus are manufactured by reaction of dialkylphosphites or alkylene phosphites of the formula I with cyclic urea derivatives containing two or more glycidyl groups, under warm conditions especially at temperatures of 100°–200°C. As a rule, the reaction does not lead to pure adducts of one mol of phosphite and one mol of a polyglycidyl compound, since the hydroxyl groups produced in this reaction frequently react further, either with a further epoxide group or with an alkoxy group of the phosphite, with elimination of alcohol. The addition reaction can be accelerated catalytically, for example with tetramethylammonium chloride.

The corresponding adducts, being epoxide resins, can be cured with customary curing agents to give infusible, insoluble shaped articles. This curing reaction can take place immediately after the adduct reaction by first mixing the dialkyl phosphite with the polyglycidyl compound and a curing agent for epoxide resins and then exposing this mixture to the customary curing temperatures.

If the adducts are isolated, they are found to have phosphorus contents of between 1 and 8 percent and epoxide contents of between 1 and 6 equivalents/kg, depending on the starting substances. The adducts range from viscous liquids to solid substances with softening points between 40° and 120°C.

The new adducts can be crosslinked and cured with the customary curing agents for epoxide resins. It is possible to use both basic and acid curing agents, that is to say amines, such as aliphatic, cycloaliphatic or aromatic primary, secondary or tertiary amines, above all polyamines, also polyamides and amine complexes with $BF_3$, and also acids, but especially the anhydrides of polybasic carboxylic acids.

The mechanical properties of the adducts cured with the acid anhydrides are as good as those displayed by the cured phosphorus-free resins on which the adducts according to the invention are based.

The curing reaction is as a rule carried out with simultaneous shaping to give shaped articles, such as castings, pressings or laminates, or to give coatings.

The curing agents together with the adducts can first be converted into a mixture which, depending on the components, can be stored for a longer or shorter period and is subsequently cured by warming. The mixture can furthermore contain the customary additives, such as reactive diluents, fillers, pigments and the like.

The adducts according to the invention, or the mixtures according to the invention, are mainly employed in the fields of the electrical industry, in laminating processes and in the building industry.

MANUFACTURING EXAMPLES

EXAMPLE 1

400 g of 1,3-diglycidyl-5,5-dimethylhydantoin of epoxide content 7.7 epoxide equivalents/kg, 86.8 g of diethyl phosphite (0.629 mol) and 0.2 ml of a 40 percent strength solution of tetramethylammonium chloride in methanol are stirred at 148°–157°C reaction temperature (bath temperature 180°C). The addition reaction is followed by determining the epoxide content of samples withdrawn from the reaction mixture. After 60 minutes reaction time the epoxide content is 5.80 epoxide equivalents/kg. The reaction is stopped after 260 minutes and the reaction product is freed of readily volatile constituents on a rotary evaporator at 110°C under a water pump vacuum. Thereafter it is dried to constant weight at 110°C and 0.1 mm Hg.

436.8 g of a yellow, clear, viscous resin having an epoxide content of 4.85 epoxide equivalents/kg and a phosphorus content of 3.77% P are obtained.

The IR spectrum shows the absence of the P-H band (there is a distinct P-H band of the reaction mixture, prior to the addition reaction, at 2,410 cm⁻¹) and the presence of the OH band at 2,880 cm⁻¹. The volatile constituents removed from the reaction product contain about 40 percent of ethanol, which is determined by fractional distillation through a rotating strip column. This ethanol is produced by trans-esterification of the hydroxyl groups, formed in the addition reaction, with the ethoxyphosphorono groups. This is also confirmed by analysis of the resin by gel chromatography which shows the presence of approx. 35 percent of a 1:1 adduct of 1,3-diglycidyl-5,5-dimethylhydantoin and diethyl phosphite and of approx. 65 percent of oligomers of molecular weight about 2,500.

EXAMPLE 2

A mixture of 100 g of an industrially manufactured triglycidyl compound produced from 1,3-bis-(5,5-dimethylhydantoinyl-3)-propan-2-ol and having an epoxide content of 6.15 epoxide equivalents/kg, 21.7 g of diethyl phosphite (0.157 mol) and 0.05 ml of 50 percent strength aqueous sodium hydroxide solution is reacted at 140°–156°C (bath temperature 170°C). The decrease in epoxide content during the addition reaction is followed analogously to Example 1. The epoxide content is 4.15 epoxide equivalents/kg after 85 minutes reaction time and 3.93 epoxide equivalents/kg after 145 minutes. The reaction is complete after 135 minutes and working up takes place as in Example 1 by removing the volatile constituents on a rotary evaporator at 130°C.

102.3 g of a brittle yellow resin of epoxide content 3.73 epoxide equivalents/kg and phosphorus content 4.03% P are obtained. The softening point is 50°C.

EXAMPLE 3

200 g of industrially manufactured 1-(glycidyloxymethyl)-3-glycidyl-5,5-dimethylhydantoin, having an epoxide content of 7.2 epoxide equivalents/kg, 66.7 g of di-n-butylphosphite (0.343 mol) and 0.2 ml of a 40% strength solution of tetramethylammonium chloride in methanol are reacted at 160°–171°C. The reaction is complete after 155 minutes and after working up according to Example 1, 237 g of a brown, clear, highly viscous resin with 3.32 epoxide equivalents/kg and a phosphorus content of 4.39%, P are obtained.

EXAMPLE 4

300 g of 1,3-diglycidyl-5,5-pentamethylenehydantoin having an epoxide content of 7.11 epoxide equivalents/kg, 65.3 g of diethyl phosphite (0.473 mol) and 0.2 ml of a 40% strength solution of tetramethylammonium chloride in methanol are stirred for 215 minutes at 150°–167°C (bath temperature 180°C). Working up takes place analogously to Example 1 and 333.4 g of a clear, brownish, very highly viscous resin with 4.37 epoxide equivalents/kg and a phosphorus content of 3.97% P are obtained.

EXAMPLE 5

500 g of bis-(3-glycidyl-5,5-dimethylhydantoinyl-1)-methane having an epoxide content of 5.1 epoxide equivalents/kg, 108.7 g of diethyl phosphite (0.787 mol) and 0.5 ml of a 40% strength solution of tetramethylammonium chloride in methanol are reacted at 156°–160°C (bath temperature 170°–180°C). After 277 minutes, 0.5 ml of a 40% strength solution of tetramethylammonium chloride in methanol is added. The reaction is stopped after 400 minutes and volatile constituents are removed on a rotary evaporator at 150°C, analogously to Example 1. 531 g of a yellow, brittle resin with 2.74 epoxide equivalents/kg, a phosphorus content of 3.81% P and a softening point of 90°C are obtained.

EXAMPLE 6

A mixture of 100 g of 1,3-diglycidyl-tetrahydrobenzimidazolidone (epoxide content: 7.4 epoxide equivalents/kg) and 21.75 g of diethyl phosphite (0.1575 mol) is allowed to react for 1 hour at 106°–120°C internal temperature. After working up the reaction mixture analogously to Example 1, 107.3 g of a brownish, highly viscous resin with 4.62 epoxide equivalents/kg and a phosphorus content of 3.95% P are obtained.

EXAMPLE 7

400 g of 1,3-diglycidyl-5,5-dimethylhydantoin (epoxide content: 7.7 epoxide equivalents/kg), 76.2 g of dimethyl phosphite (0.614 mol) and 0.2 ml of a 40% strength solution of tetramethylammonium chloride in methanol are stirred at 146°–163°C (bath temperature 185°C) for 100 minutes. The reaction product is worked up analogously to Example 1. A yellow, clear, highly viscous resin is obtained, which contains 4.82 epoxide equivalents/kg and 4.45% of phosphorus.

USE EXAMPLES

I 100 g of epoxide resin (manufactured according to Example 1) and 71.0 g of hexahydrophthalic anhydride are converted to a clear, homogeneous melt at 120°C. This mixture is poured into aluminium moulds of size 120 × 120 × 4 mm and 120 × 15 × 10 mm prewarmed to 120°C. The resin is cured in 2 hours at 120°C and 16 hours at 150°C. The mouldings thus obtained display the following mechanical properties:

| | |
|---|---|
| Flexural strength (VSM 77,103) | 13.6–14.7 kp/mm² |
| Deflection (VSM 77,103) | 7.1–9.7 mm |
| Impact strength (VSM 77,105) | 12.8–15.0 cmkp/cm² |
| Heat distortion point according to Martens (DIN 53,458) | 139°C |
| Inflammability according to CTM 20* | Level 1 (6″) |
| Water absorption (4 days/20°C) | 0.88% |
| Water absorption (1 hour/100°C) | 0.41% |

*CTM 20: Description of the test: A horizontally clamped DIN standard bar (120×15×10 mm) of the plastic to be tested is exposed for 1 minute to the flame of a bunsen burner inclined at 45° and fed with town gas (burner orifice: 9 mm, height of flame with burner vertical: 10 cm), so that the 15 mm wide surface of the test specimen is 3 cm above the upper edge of the burner and the end face is at a distance of 1 cm, in the horizontal direction, from the lower edge of the burner. Level 1 means that after removing the flame the bar continues to burn for not more than 15 seconds. It is comparable with category 2 of ISO/R 1,210 (duration of burning 0–15 seconds).

II 100 g of epoxide resin (manufactured according to Example 2) and 48.8 g of hexahydrophthalic anhydride at 120°C are mixed, cast and cured analogously to Use Example I. The test of the mouldings yields the following data:

| | |
|---|---|
| Flexural stress (VSM 77,103): | 6.6–9.5 kp/mm² |
| Deflection (VSM 77,103): | 2.7–3.7 mm |
| Impact strength (VSM 77,105): | 5.0–6.9 cmkp/cm² |
| Heat distortion point according to Martens (DIN 55,458) | 129°C |
| Inflammability according to CTM 20 | Level 1 (12″) |
| Water absorption (1 hour/100°C) | 2.2% |

III 100 g of epoxide compound (manufactured according to Example 3) and 48.8 g of hexahydrophthalic anhydride are processed analogously to Use Example I. The following mechanical properties are found:

| | |
|---|---|
| Flexural strength (VSM 77,103) | 13.6–15.1 kp/mm² |
| Deflection (VSM 77,103) | 7.1–9.5 mm |
| Impact strength (VSM 77,105) | 8.5–12.5 cmkp/cm² |
| Heat distortion point according to Martens (DIN 53,458) | 109°C |
| Inflammability according to CTM 20 | Level 1 (3″) |
| Water absorption (4 days/20°C) | 0.93% |

IV 100 g of epoxide resin (manufactured according to Example 4) are stirred with 64.0 g of hexahydrophthalic anhydride at 120°C to give a homogeneous solution, the mixture is cast and cured analogously to Use Example I, and mouldings having the following mechanical properties are thus obtained:

| | |
|---|---|
| Flexural strength (VSM 77,103) | 8.8–11.0 kp/mm² |
| Deflection (VSM 77,103) | 3.8–4.8 mm |
| Impact strength (VSM 77,105) | 5.3–11.0 cmkp/cm² |
| Heat distortion point according to Martens (DIN 53,458) | 137°C |
| Inflammability according to CTM 20 | Level 1 (2″) |
| Water absorption (4 days/20°C) | 0.57% |
| Water absorption (1 hour/100°C) | 0.80% |

V 100 g of resin (manufactured according to Example 5) and 40.1 g of hexahydrophthalic anhydride are processed analogously to Use Example 1. The mouldings thus obtained show the following properties:

| | |
|---|---|
| Heat distortion point according to Martens (DIN 53,458) | 145°C |
| Inflammability according to CTM 20 | Level 0 (18″) |

VI

A mixture of 100 g of epoxide resin (manufactured according to Example 7) and 70.5 g of hexahydrophthalic anhydride is cast at 120°C and cured, analogously to Example I.

Mechanical properties:

| | |
|---|---|
| Flexural strength (VSM 77,103) | 11.6–16.7 kp/mm² |
| Deflection (VSM 77,103) | 8.4–9.2 mm |
| Impact strength (VSM 77,105) | 12.0–14.0 cmkp/mm² |
| Heat distortion point according to Martens (DIN 53,458) | 144°C |
| Inflammability according to CTM 20 | Level 1 (0″) |
| Water absorption (4 days/20°C) | 0.82% |

VII

A mixture of 100 g of epoxide compound manufactured according to Example 4 and 21.6 g of 4,4′-diamino-diphenylmethane is stirred at 80°C to give a homogeneous mixture, poured into aluminium moulds prewarmed to 80°C and cured for 4 hours at 80°C and 6 hours at 140°C.

Test results

| | |
|---|---|
| Flexural strength (VSM 77,103) | 14.1–18.0 kg/mm² |
| Deflection (VSM 77,103) | 6.3–6.8 mm |
| Impact strength (VSM 77,105) | 10.8–17.3 cmkg/cm² |
| Heat distortion point according to Martens (DIN 53,461) | 163°C |
| Inflammability according to CTM 20 | Level 1 (7″) |
| Water absorption (4 days/20°C) | 0.84% |

We claim:

1. An adduct prepared by reacting a hydantoin compound selected from the group consisting of 1,3-diglycidyl-5,5-dimethylhydantoin, the triglycidyl compound produced from 1,3-bis-(5,5-dimethylhydantoinyl-3)-propan-2-ol, 1-(glycidyloxymethyl)-3-glycidyl-5,5-dimethylhydantoin, 1,3-diglycidyl-5,5-pentamethylenehydantoin, bis-(3-glycidyl-5,5-dimethylhydantoinyl-1)-methane and 1,3-diglycidyl-5,5-dimethylhydantoin, and a compound of the formula I $$\begin{array}{c} R_1-O \\ R_2-O \end{array} P \begin{array}{c} O \\ H \end{array} \qquad (I)$$

wherein $R_1$ and $R_2$ each represent an alkyl of 1 to 4 carbon atoms, monochloroethyl or together form an alkylene of to 5 carbon atoms, wherein said adduct contains from 1 to 8% phosphorus and has an epoxide content between 1 to 6 equivalents/kg.

2. An adduct according to claim 1 prepared in the presence of tetramethlammonium chloride.

3. A compound according to claim 1, characterised in that $R_1$ and $R_2$ each denote the methyl, ethyl or propyl group or a monochloroethyl group.

* * * * *